US009034095B2

(12) United States Patent
Tsuchiya et al.

(10) Patent No.: US 9,034,095 B2
(45) Date of Patent: May 19, 2015

(54) GREENISH BLUE PIGMENT, COLORANT COMPOSITION CONTAINING SAID PIGMENT, AND IMAGE RECORDING MATERIAL

(75) Inventors: Koji Tsuchiya, Tokyo (JP); Masahiko Aoba, Tokyo (JP); Kenjiro Matsumoto, Tokyo (JP); Takeshi Tamaki, Tokyo (JP)

(73) Assignee: DAINICHISEIKA COLOR & CHEMICALS MFG. CO., LTD., Tokyo (JP)

( * ) Notice: Subject to any disclaimer, the term of this patent is extended or adjusted under 35 U.S.C. 154(b) by 0 days.

(21) Appl. No.: 14/234,345

(22) PCT Filed: Jul. 19, 2012

(86) PCT No.: PCT/JP2012/068264
§ 371 (c)(1),
(2), (4) Date: Jan. 22, 2014

(87) PCT Pub. No.: WO2013/015180
PCT Pub. Date: Jan. 31, 2013

(65) Prior Publication Data
US 2014/0150692 A1   Jun. 5, 2014

(30) Foreign Application Priority Data
Jul. 22, 2011  (JP) .................................. 2011-161251

(51) Int. Cl.
| C09B 47/24 | (2006.01) |
| C09B 67/46 | (2006.01) |
| B41J 2/01 | (2006.01) |
| C09D 11/00 | (2014.01) |
| B41M 5/00 | (2006.01) |
| G02B 5/20 | (2006.01) |
| G02B 5/22 | (2006.01) |
| C09B 67/20 | (2006.01) |
| C07F 1/08 | (2006.01) |
| C09B 47/16 | (2006.01) |
| C09D 7/00 | (2006.01) |
| C09D 11/322 | (2014.01) |

(52) U.S. Cl.
CPC . C07F 1/08 (2013.01); C09B 47/16 (2013.01); G02B 5/223 (2013.01); C09D 7/007 (2013.01); C09D 11/322 (2013.01)

(58) Field of Classification Search
USPC .......... 106/410, 413; 540/122, 131, 135, 139, 540/140
See application file for complete search history.

(56) References Cited

U.S. PATENT DOCUMENTS

| 2,761,868 | A |   | 9/1956 | Lacey ........................... 540/123 |
| 2,855,403 | A | * | 10/1958 | McKellin et al. ............. 540/123 |
| 3,589,924 | A |   | 6/1971 | Giambalvo et al. ........... 106/411 |
| 4,448,607 | A | * | 5/1984 | Johnson et al. ............... 106/411 |
| 4,518,672 | A | * | 5/1985 | Urawa et al. ............. 430/108.21 |
| 5,264,032 | A | * | 11/1993 | Dietz et al. .................... 106/411 |
| 5,820,962 | A | * | 10/1998 | Kimura et al. ............... 428/64.1 |
| 6,391,507 | B1 | * | 5/2002 | Macholdt et al. ........ 430/108.24 |
| 6,406,528 | B1 | * | 6/2002 | Macholdt et al. .......... 106/31.49 |
| 6,468,341 | B2 | * | 10/2002 | Wada et al. .................... 106/413 |
| 7,232,853 | B2 | * | 6/2007 | Nakamura et al. ................ 524/1 |
| 2009/0293769 | A1 |   | 12/2009 | Lee et al. ....................... 106/411 |
| 2012/0010400 | A1 | * | 1/2012 | Chen et al. .................... 540/123 |

FOREIGN PATENT DOCUMENTS

| CN | 101627089 | 1/2010 |
| JP | 58-203455 | 11/1983 |
| JP | 6-100787 | 4/1994 |
| JP | 2002-80745 | 3/2002 |
| JP | 2003-147224 | 5/2003 |
| JP | 2008-248112 | 10/2008 |
| JP | 2009-151162 | 7/2009 |
| JP | 2009-173800 | 8/2009 |

* cited by examiner

Primary Examiner — Anthony J Green
(74) Attorney, Agent, or Firm — Hamre, Schumann, Mueller & Larson, P.C.

(57) ABSTRACT

An object is to overcome the drawbacks of conventional blue phthalocyanine pigments upon the formation of images, and to develop a blue pigment that can satisfactorily exhibit a greenish blue color high in chroma and excellent in colorfulness, brightness, dispersibility, hue, tinting power and the like and that is applicable to various image recording methods. The object can be achieved by a greenish blue pigment, which exhibits a greenish blue hue of high chroma and contains a pigment represented by the following formula (I):

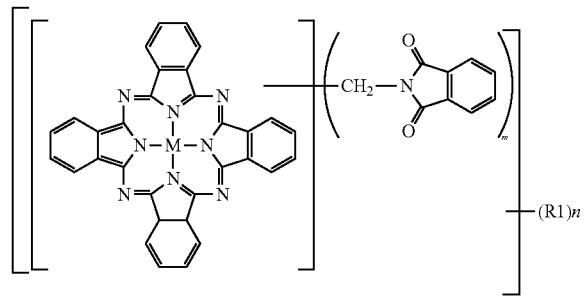

wherein the number, m, of substituent phthalimidomethyl group(s) is in a range of $1.0 \le m \le 5.0$, and the number, n, of a substituent sulfonic group R1 is in a range of $0.05 \le n \le 1.0$.

8 Claims, No Drawings

GREENISH BLUE PIGMENT, COLORANT COMPOSITION CONTAINING SAID PIGMENT, AND IMAGE RECORDING MATERIAL

TECHNICAL FIELD

This invention relates to a greenish blue pigment exhibiting a greenish blue hue of high chroma, and a colorant composition and image recording material containing the pigment.

BACKGROUND ART

Copper phthalocyanine pigments are a series of excellent pigments, and feature having a colorful blue shade and various superb fastness or resistance properties. In particular, C.I. Pigment Blue 15:3 (hereinafter abbreviated as "PB15:3") and dispersion-stabilized C.I. Pigment Blue 15:4 (hereinafter abbreviated as "PB15:4"), which are both in the form of β crystals, are each abundantly used as cyan color, one of the three primary colors employed in process printing, over years. In recent years, however, the use of pigments as colorants is spreading in a variety of new image recording methods, led by the electrophotographic recording method, inkjet recording method and thermal transfer recording method, in addition to the conventional printing method using a machine plate. In such applications, requirements different from those required conventionally have arisen for cyan color. Described specifically, these recording methods have imposed, for the realization of still better color reproducibility upon formation of images, new keen requirements for a pigment, which has a bluish green color as a substitute cyan color for conventional copper phthalocyanines of blue color, and also for a colorant making use of the pigment and enabling high-chroma, colorful image recording (which may hereinafter be called an "image recording material").

The above-described conventional copper phthalocyanine pigments (PB15:3 and PB15:4) are excellent in dispersibility, density, light fastness, heat resistance, electrostatic chargeability and safety. Nonetheless, they are too reddish than a desired cyan color when used singly, and may hence be used in combination with C.I. Pigment Green 7, C.I. Pigment Green 36, C.I. Pigment Green 58 or the like to correct their colors. In such a case, however, colors of considerably different hues are subjected to subtractive color mixing so that the resulting image tends to be provided with reduced chroma. Moreover, there is also a problem of load on the environment upon disposal because the above-described pigments to be used in combination contain halogen atoms in their structures.

Known cyan pigments other than the above-described, conventional copper phthalocyanine pigments include those to be described hereinafter. Phthalimidomethyl derivatives and the like of copper phthalocyanine are described in Patent Document 1. However, no description is made about their synthesis processes in Patent Document 1. When the present inventors synthesized these pigments in a manner known per se in the art, no tinting power inherent to the pigments was obtained due to the inclusion of impurities in large amounts, and the pigments were low in chroma. It was, therefore, impossible to obtain colorful images. Patent Document 2 describes a formula representing a phthalimidomethyl derivative, which may contain desired substituent group(s), as a copper phthalocyanine derivative having a substituent group on one or more benzene rings. However, the derivative called "PIM", which is described in one of the comparative examples, contains no substituent group other than a phthalimidomethyl group on the phthalocyanine structure, and there is no example in which any other substituent group or groups are used. Obviously, no description is made about the color features of such derivatives. Mixtures of copper phthalocyanine and nickel phthalocyanine as described in Patent Documents 3 and 4 are not practically usable in applications such as toners for electrophotographic recording and inks for inkjet recording, because nickel phthalocyanine is a material having a problem in safety.

Patent Document 5 describes a copper phthalocyanine having phthalimidomethyl group(s), and specifies that the number of the phthalimidomethyl group(s) is 0.6 to 2.1, the number of sulfonic group(s) is 0.2 to 2.5, and as an additional essential requirement, the sum of these numbers is not greater than 3. However, the above material described in Patent Document 5 is intended as a crystal growth inhibitor or dispersion stabilizer for pigments, and Patent Document 5 contains no disclosure about a pigment exhibiting a bluish blue hue of high chroma such as that intended in the present invention.

Patent Document 6 discloses a process that reacts paraformaldehyde and phthalimide or a substituted phthalimide with copper phthalocyanine, a process that reacts copper phthalocyanine with bis-phthalimidomethyl ether or a substituted bis-phthalimidomethyl ether, and a process that reacts copper phthalocyanine with N-hydroxymethylphthalimide or a substituted N-hydroxymethylphthalimide, all, in an acidic solvent such as concentrated sulfuric acid. No description is, however, made about a sulfonated, phthalimido-containing phthalocyanine derivative in its examples.

Copper phthalocyanine pigments are extremely good in the shade, tinting power and various fastness or resistance properties of a colorful blue color compared with other blue pigments. Attempts have, however, been made in recent years to change copper, which is a heavy metal, to other metals or non-metals. In Patent Document 7 and the like, various pigments are proposed, including those which have been put into commercial products. Even with these non-copper, metal phthalocyanines pigments or non-metal phthalocyanine pigments, no bluish green pigments have, however, been realized to fully meet such a greenish blue hue of high chroma as mentioned above and long-awaited in the recent new recording methods.

PRIOR ART DOCUMENTS

Patent Documents

Patent Document 1: JP-A-58-203455
Patent Document 2: JP-A-2002-80745
Patent Document 3: JP-A-2009-151162
Patent Document 4: JP-A-2009-173800
Patent Document 5: U.S. Pat. No. 3,589,924
Patent Document 6: U.S. Pat. No. 2,761,868
Patent Document 7: JP-A-6-100787

DISCLOSURE OF THE INVENTION

Problem to be Solved by the Invention

As has been described above, none of the conventional pigments are satisfactory as colorants to be used for a cyan color required in image recording materials for use in new image recording methods, the developments of which are pronounced in recent years, such as those mentioned above, more specifically as pigments exhibiting a greenish blue hue of high chroma such as that long-awaited in these recording methods. There is, accordingly, an outstanding desire for the development of a greenish blue pigment of high chroma, which has physical properties applicable to various recording methods and can be used as a cyan color for an image recording material.

Therefore, an object of the present invention is to resolve the drawbacks of the conventional cyan pigments for image recording materials, and to develop a pigment which is excellent in safety, has physical properties applicable to various recording methods and can meet a greenish blue color of high chroma. Another object of the present invention is to provide an excellent image recording material, which is applicable to various recording methods the developments of which are pronounced to find wide-spread utility in recent years and which is free of any safety problem when disposed of, by obtaining, owing to the development of such a pigment, a colorant composition capable of exhibiting properties excellent in the colorfulness, brightness, transparency and the like of a hue and then using the colorant composition.

Means for Solving the Problem

The above-described objects can be achieved by the present invention to be described hereinafter. Described specifically, the present invention provides a greenish blue pigment exhibiting a greenish blue hue of high chroma and comprising a pigment represented by the following formula (I):

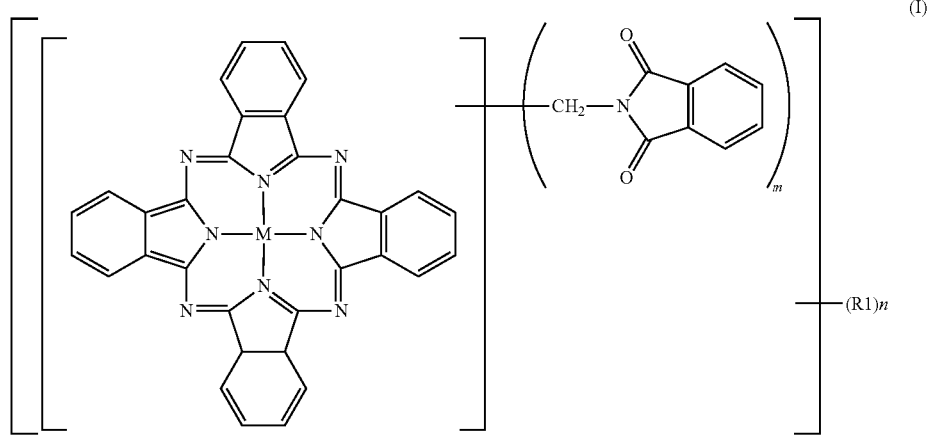

wherein m indicates the number of phthalimidomethyl group(s), m is in a range of $1.0 \leq m \leq 5.0$, R1 represents a sulfonic group, n indicates the number of the substituent group, n is in a range of $0.05 \leq n \leq 1.0$, and M is a liganded or unliganded metal atom of Cu, Al or Zn. It is to be noted that the term "liganded or unliganded" as used herein means that a metal atom of Cu, Al or Zn may have one or more ligands.

Preferred embodiments of the greenish blue pigment according to the present invention can include the followings: the greenish blue pigment, wherein the pigment represented by the formula (I) has a purity of at least 95.0%; the greenish blue pigment, wherein in the formula (I), m is in a range of $2.5 \leq m \leq 4.0$ and n is in a range of $0.05 \leq n \leq 0.7$; and the greenish blue pigment, wherein in a spectral reflectance spectrum of the greenish blue pigment, a maximum reflectance spectrum in a visible light range of 380 nm to 780 nm exists in a range of 460 nm to 500 nm.

As a still further embodiment, the present invention also provides a colorant composition comprising at least a pigment and a resin, wherein the pigment comprises any one of the above-described greenish blue pigments.

As an even further embodiment, the present invention also provides an image recording material useful in a recording method selected from electrophotography, electronic printing, electrostatic recording or thermal transfer recording, comprising any one of the above-described greenish blue pigments.

As yet further embodiments, the present invention also provides an image recording material for inkjet recording, comprising the above-described colorant composition, and an image recording material for a color filter, comprising the above-described colorant composition.

Advantageous Effects of the Invention

According to the present invention, there is provided a novel blue pigment, which has resolved the drawbacks of the conventional cyan pigments for image recoding materials, is excellent in safety, and exhibits a greenish blue hue of high chroma. Under the circumstances of the existence of, for example, the PIM (phthalimidomethylated) derivative described in Patent Document 2, the nickel phthalocyanines described in Patent Documents 3 and 4, the products available from Nippon Kayaku Co., Ltd., and so on, the present invention has realized the provision of a pigment, which exhibits a greenish blue hue of high chroma, by using phthalocyanine, which is excellent in physical properties especially such as light fastness, heat resistance and chemical resistance, as a basic skeleton to add its excellent physical properties, and at the same time, by specifying the kinds and numbers of its substituent groups in detail to enable control of greenishness color, said control being effective for each desired application. As reasons for this, the present inventors consider as will be described hereinafter. As the structure of the pigment that characterizes the present invention is represented by the formula (I), the characteristic crystallinity of a phthalocyanine pigment of excellent pigmentary properties can transform to have many crystalline forms such as α-form, β-form and ε-form, and these crystalline forms have characteristics excellent in blue shades such as reddishness and greenishness, respectively. Moreover, depending on the final application purpose, the control of green color balance is feasible by selecting substituent groups. As a consequence of these, the pigment is considered to have the above-described excellent features. According to the present invention, the use of the pigment represented by the formula (I) can, therefore, obtain a colorant composition that can exhibit properties excellent in the colorfulness, brightness and transparency of a hue. In addition, the use of the colorant composition makes it possible to provide an excellent image recording material, which involves no problem in safety when disposed of and can meet new desires for shades in various image forming methods the developments of which are pronounced to find wide-spread utility in recent years.

MODES FOR CARRYING OUT THE INVENTION

The present invention will hereinafter be described in further detail based on preferred embodiments for carrying out the invention.

The present inventors have conducted enthusiastic research to resolve the above-described drawbacks of the conventional technologies. As a result, the present inventors found a pigment exhibiting a bluish blue hue of high chroma and represented by the below-described formula (I), leading to the present invention. Described specifically, when the pigment developed by the present invention is used and is applied especially to an image recording material useful in various image forming methods, the utilization of which is pronounced in recent years, in place of the copper phthalocyanine pigments having a strongly reddish blue color and used abundantly as a cyan color in conventional recording methods, still better color reproducibility can be realized so that colorful images of high chroma can be provided. More specifically, the incorporation of the pigment represented by the below-described formula (I) makes it possible to provide a colorant composition that can exhibit properties excellent in the colorfulness, brightness and transparency of a hue, and moreover, the use of the colorant composition makes it possible to provide an excellent image recording material that has no problem in safety either and is applicable to various recording methods.

by the formula (I) preferably has high purity. When the pigment developed by the present invention is finally used as an image recording material, an image excellent in colorfulness, brightness, transparency and the like can be recorded. These characteristic features are preferably expressed no matter whether the image recording material is in the form of a solid or liquid.

For the synthesis of the pigment characterizing the present invention and represented by the formula (I) (which may hereinafter be also called "the pigment according to the present invention"), known processes can be used. Usable examples include a process that reacts paraformaldehyde and phthalimide or a substituted phthalimide with copper phthalocyanine, a process that reacts copper phthalocyanine with bis-phthalimidomethyl ether or a substituted bis-phthalimidomethyl ether, and a process that reacts copper phthalocyanine with N-hydroxymethylphthalimide or a substituted N-hydroxymethylphthalimide, all, in an acidic solvent such as concentrated sulfuric acid.

(Synthesis Process of Pigment)

About a process for the synthesis of the phthalocyanine derivative pigment represented by the formula (I) and characterizing the present invention, a description will hereinafter be made based on an example.

In this example, conventionally-used copper phthalocyanine is first prepared in a manner known per se in the art. The resultant copper phthalocyanine is then reacted with hydroxymethylphthalimide or with paraformaldehyde and phthalimide to phthalimidomethylate copper phthalocyanine. The reaction mixture is then heated to a high temperature to conduct sulfonation, whereby a compound represented by the formula (I) is obtained. The sulfonic group introduced in the sulfonation can be a salt with a base, to say nothing of a free sulfonic group. The base can be, for example, a metal salt (a salt with an alkali metal or a multivalent metal such as Ca, Ba, Al, Mn, Sr, Mg or Ni), the ammonium salt, an amine salt, or

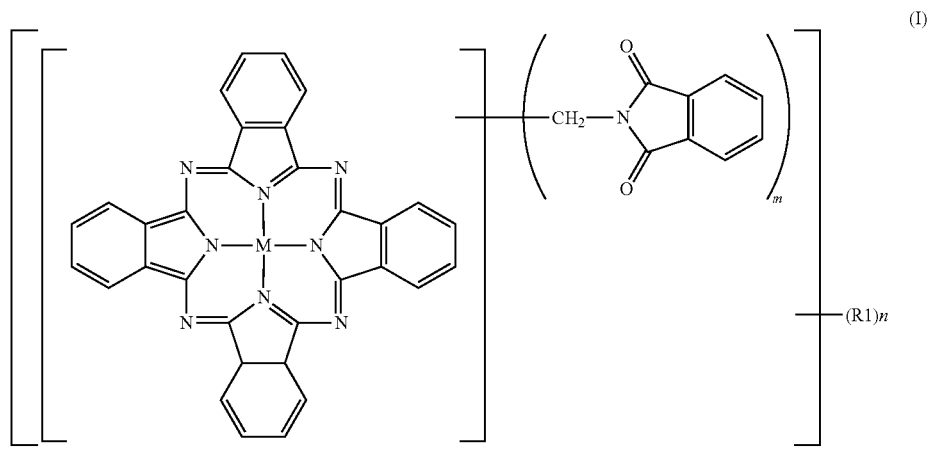

(I)

m: number of substituent phthalimidomethyl group(s), 1.0≤m≤5.0
n: number of a substituent sulfonic group, 0.05≤n≤1.0
R1: a sulfonic group
M: a liganded or unliganded metal atom of Cu, Al or Zn.

The colorant composition and image recording material according to the present invention are characterized by containing the pigment represented by the above-described formula (I). The pigment component in the pigment represented a mixture thereof. As an amine that forms the amine salt, a (mono, di or tri)alkylamine, a substituted or unsubstituted alkylenediamine, an alkanolamine, an alkylammonium chloride or the like can be used.

Similar to the foregoing, N-hydroxymethylphthalimide to be used as described above can be synthesized in a manner known per se in the art. In the present invention, one synthesized as will be described hereinafter was used. Phthalimide and formalin were added, followed by heating at 90 to 100° C.

under stirring. The synthesized product was obtained by filtration, washing and drying under reduced pressure. As infrared absorption peaks were observed at 3,480 cm$^{-1}$ (OH group) and 1,780 and 1,720 cm$^{-1}$ (C=O groups) by the infrared spectroscopic analysis method (IR) and the melting point was 143 to 146° C. (literature value: 142 to 145° C.), the synthesized product was identified to be N-hydroxymethylphthalimide.

In the foregoing, the description was made by taking, as an example, the case in which M in the formula (I) is copper. The present invention is, however, not limited to such a case, and M in the formula (I) can be a liganded or unliganded metal atom of Cu, Al or Zn. Specific examples include tetraamine copper complex, copper, zinc, and aluminum. In particular, one having copper as M can be preferably used because it is stable in versatility and production process and is excellent in weatherability. However, M is not necessarily limited to copper, and a colorful blue pigment exhibiting a greenish blue or bluish green hue as intended in the present invention can be equally achieved no matter which one of the above-described metals is M in the formula (I). In such a case, known aluminum phthalocyanine or zinc phthalocyanine can be used instead of copper phthalocyanine. These phthalocyanines can be produced in a manner known per se in the art, for example, by a method that substitutes aluminum or the like for the copper in copper phthalocyanine or a method that coordinates aluminum or the like in metal-free phthalocyanine.

(Calculation Method of the Purity of Pigment)

The purity of the pigment was determined by adopting acetonitrile as an extraction solvent and conducting extraction treatment by the Soxhlet method under the below-described conditions. Acetonitrile was adopted as it dissolves impurities, i.e., N-hydroxymethylphthalimide, phthalimide, phthalic acid and the like without dissolution of the synthesized phthalocyanine derivative represented by the formula (I).

With respect to the phthalocyanine derivative synthesized as described above, extraction was conducted by the Soxhlet method under the following conditions.

Extraction solvent: acetonitrile, 100 mL
Sample: synthesized phthalocyanine derivative, 10.0 g
Distillation rate: 50 mL/7 min
Extraction time: weight loss was measured over 3 to 28 hours.

As no weight loss was observed at and after the 8$^{th}$ hour, the extraction was considered to have been substantially completed within 8 hours, and every extraction time was set uniformly for 10 hours. After the extraction, the phthalocyanine derivative was collected by filtration through a glass filter, thoroughly washed with acetonitrile, and dried at 105° C. for 5 hours to obtain a purified sample. As a consequence, the purity of the synthesized pigment can be determined by the following equation.

Purity(mass %)=(number of grams of the pigment dried after extraction with acetonitrile for 10 hours)×100/10.0 g According to a study by the present inventors, the purity of the pigment obtained as described above becomes a particularly important factor in the colorfulness, brightness, transparency, tinting power and the like of a hue in connection with its final application as a colorant. Further, as will be mentioned below, effects due to the existence of impurities are not limited to such a factor. It is, therefore, preferred to use one having a purity as high as possible. When the pigment according to the present invention is synthesized by such a process as described above, impurities contained in the synthesized phthalocyanine derivative are primarily phthalimide, which was used as a raw material and is remaining unreacted, and phthalimide-based impurities (those formed through reactions of phthalimide or N-hydroxymethylphthalimide itself) formed during the reaction. As these impurities have low solubility in organic solvents, the impurities themselves form hard agglomerates as time goes on and become a cause of poor dispersion when subjected to dispersion, for example, in a wet media disperser, which makes use of beads, in a subsequent pigmentation step. It is, therefore, necessary to reduce the amount of impurities as much as possible. Effects of the mixing of such agglomerates include those to be described below.

When an image recording material with such a pigment contained therein is used for an inkjet application, for example, there is a potential problem in that the impurities may deposit around or inside a nozzle of an inkjet head and may adversely affect the ejection of the ink. When the image recording material is used in a color toner application for electrophotographic recording, on the other hand, the presence of abundant impurities obviously leads to a reduction in image tinting power, and the impurities deposited on a printer drum also become a cause of machine troubles. It is, however, preferred to achieve the optimization of purity and quality in commensurate with the final application while also taking into consideration the degree of purification of the pigment to be used and the cost aspects of the production process. For use or the like with a limited purpose or effect, it is sufficient for a purpose or effect other than the above-mentioned purpose or effect if the purpose or effect can be achieved to such an extent as available from ordinary copper phthalocyanine. From the viewpoint of the effects to be expressed as the phthalocyanine derivative, purities of 90% and so are still sufficiently effective. More preferably, however, the purity of the pigment determined as described above may be 95% or higher in that still higher effects on such colorfulness, brightness, transparency, tinting power and the like as mentioned above can be stably obtained.

(Control Method of the Numbers of Respective Kinds of Substituent Groups to be Introduced onto Phthalocyanine Skeleton)

Phthalimidomethyl group(s) are generally introduced by reacting phthalocyanine with hydroxymethylphthalimide or with paraformaldehyde and phthalimide in sulfuric acid or fumed sulfuric acid. The reaction with hydroxymethylphthalimide is preferred from the readiness of control of the number of the substituent group(s). Upon conducting the reaction, the reaction temperature is generally 70° C. or higher. As the number of moles of hydroxymethyl phthalimide to be used becomes greater relative to phthalocyanine, the number of introduced phthalimidomethyl group(s) increases, but unreacted hydroxymethylphthalimide also increases to lower the purity and to become as a cause of a lowered tinting power as a colorant. Care must be exercised accordingly. Unreacted hydroxymethylphthalimide can be eliminated by conducting treatment with a dilute alkali of such strength that the introduced phthalimidomethyl group(s) are not hydrolyzed, so that the purity can be increased. Further, a higher reaction temperature leads to a higher reactivity, and as a result, to a higher purity. However, sulfonation also takes place at the same time if the reaction temperature is raised to 90° C. or higher. The reaction can be conducted either by a two-step process that phthalimidomethylation or sulfonation is conducted first and the reaction temperature is then raised or lowered to conduct sulfonation or phthalimidomethylation, or by a single-step process that phthalimidomethylation and sulfonation are conducted concurrently. By controlling the concentration of sulfuric acid, the usage amount of hydroxymethylphthalimide, the reaction temperature and the reaction time as described above, the derivative can be obtained with the specific substituent groups introduced in desired numbers within the corresponding ranges specified in the present invention.

(Calculation Method of the Numbers of Respective Kinds of Substituent Groups Introduced on Phthalocyanine Skeleton)

Assume that the mass of crude phthalocyanine used as a production raw material for the pigment according to the present invention is A1, its purity is P1 mass %, the mass of the phthalocyanine derivative synthesized in such a manner as described above is A2, and its purity is P2 mass %. Also assume that the mass % of sulfur as determined by an X-ray fluorescence analysis and elemental analysis is S mass %. From these values, the numbers of the respective kinds of substituent groups in the phthalocyanine derivative can be calculated by the following equations:

$$\text{Number of sulfonic group}, n = (A2 \times P2/A1 \times P1) \times 576 \times S/3200$$

$$\text{Number of phthalimidomethyl group(s)}, m = \{(A2 \times P2/A1 \times P1) \times 576 - 576 - 80 \times n\}/159$$

According to another study by the present inventors, the optimal control of the numbers of the respective kinds of substituent groups in the phthalocyanine derivative represented by the formula (I) as specified in the present invention becomes an important factor relating not only to the physical properties of the pigment itself but also directly to the expression of physical properties specific to an image recording method to which an image recording material making use of the pigment is applied. As a result of a further enthusiastic study from such a viewpoint, the pigment was found to provide a sufficient reflection density and also to exhibit a colorful, greenish blue color when it was controlled such that as specified in the present invention, the number m of substituent phthalimidomethyl group(s) falls within the range of $1.0 \leq m \leq 5.0$ and the number n of substituent sulfonic group falls within the range of $0.05 \leq n \leq 1.0$. That finding has led to the present invention. In a preferred embodiment of the present invention, the numbers m and n of the respective kinds of substituent groups in the phthalocyanine derivative, which is represented by the formula (I) and enables the designing of a green color of higher chroma and extraordinary colorfulness, are $2.5 \leq m \leq 4.0$ and $0.05 \leq n \leq 0.7$, respectively. By specifying as described above, a particularly colorful, greenish blue pigment can be obtained. It is, however, to be noted that, in any one of the ranges specified in the present invention, the phthalocyanine derivative has a distinctly colorful greenishness compared with copper phthalocyanine extensively used as a blue pigment for its excellent properties, and moreover, is by no means inferior to conventional pigments and is good in tinting power and dispersibility.

If the numbers of the respective kinds of substituent groups in the phthalocyanine derivative represented by the formula (I) are outside the corresponding ranges specified in the present invention, on the other hand, problems arise as will be described below. For example, m smaller than 1 results in insufficient colorfulness, while m greater than 5 causes a reduction in reflection density. Further, n smaller than 0.05 results in weak greenishness, while n greater than 1 allows greenish dullness to appear specifically and strongly. In such a case, the hue can be hardly adjusted by the number m of substituent group(s) so that no colorful greenish blue color can be obtained. If the numbers of the respective kinds of substituent groups are outside the corresponding ranges specified in the present invention, the pigment is, as described above, not sufficient as a pigment that exhibits a greenish blue hue of high chroma as intended in the present invention.

The pigment that characterizes the present invention is the phthalocyanine derivative having the structure represented by the formula (I). By suitably controlling m and n that indicate the numbers of the respective kinds of substituent groups in the formula (I), colorful greenishness commensurate with a purpose such as an application can be realized, and moreover, the use of the pigment makes it possible to obtain a composition excellent in tinting power and dispersibility. Especially as examples of a more effective method for the adjustment of the hue, said adjustment being achievable by suitably controlling m and n, these values may be specified as will be described hereinafter. More preferred, colorful greenishness can be obtained, for example, by controlling the numbers m and n of the respective kinds of substituent groups in the phthalocyanine derivative represented by the formula (I) such that n is controlled to $0.05 \leq n \leq 0.7$ when m is in the range of $1.0 \leq m < 2.5$ (one that satisfies these conditions will be called "B") or n is similarly controlled to $0.05 \leq n \leq 0.7$ when m is in a range of $4.0 < m \leq 5.0$ (one that satisfies these conditions will be called "G"). A pigment of preferred hue and greenishness was also confirmed to be obtainable when the number of phthalimidomethyl groups is conversely controlled to a range of $2.5 \leq m \leq 4.0$ when the number n of sulfonic group is $0.7 < n \leq 1.0$ (one that satisfies these conditions will be called "D"). In addition, when the pigment (B) in which m and n had been controlled to $1.0 \leq m < 2.5$ and $0.05 \leq n \leq 0.7$, respectively, was compared with one in which m has been changed to a range of $2.5 \leq m \leq 4.0$ and n has been controlled to a range of $0.05 \leq n \leq 0.7$, the latter was also confirmed to be a pigment of higher chroma and colorful greenishness.

The hue of the pigment that the numbers of the respective kinds of substituent groups, which make up the phthalocyanine derivative having the structure represented by the formula (I), are controlled to the corresponding ranges specified in the present invention is extremely clearly different even to the vision compared with blue copper phthalocyanine pigment most commonly used to date, and exhibits a greenish blue hue of high chroma. This difference in hue can also be evaluated by the below-described method instead of visual observation. The structure of the pigment, which is represented by the formula (I) specified in the present invention and can bring about the advantageous effects of the present invention, has been found by conducting a study according to the below-described evaluation method in addition to the visual evaluation.

As one of indices that represent hue effects, there is spectral reflectance available by spectrophotometric colorimetry. By calculating chromaticity coordinates, specifically $L^*$, $a^*$, $b^*$ values and $C^*$ value from numerical values of spectral reflectance, the difference in hue can be evaluated as will be described below. Further, the numerical value calculated by the addition of respective absolute values ($|a^*|+|b^*|$) can serve as an index of chroma. Described specifically, these numerical values serve as indices indicating that the hue becomes more greenish as the $a^*$ value becomes more negative, its chroma decreases as the $a^*$ value becomes closer to 0, the hue becomes more bluish as the $b^*$ value becomes more negative, its chroma also decreases as the $b^*$ value becomes closer to 0, and its chroma becomes higher as the $a^*$ value and $b^*$ values both increase. As described above, these values can serve as definite and objective evaluation standards for differences in hue. In the present invention, the evaluation of hues was, therefore, conducted using these values in addition to visual evaluation.

Using the evaluation method, the present inventors systematically studied about differences in hue, which occur by differences in m and n in the structure of the pigment represented by the formula (I). As a result, the ranges of the numbers of the respective kinds of substituent groups, said ranges being effective especially for the colorfulness, brightness, transparency and tinting power of a hue and also for dispersibility, have been found to be $1.0 \leq m \leq 5.0$ and $0.05 \leq n \leq 1.0$. Focusing attention on hue in particular out of these color properties, an excellent greenishness effect of $a^* \leq -25$ was exhibited when $2.5 \leq m \leq 5.0$ (D, G). On the other hand, an excellent bluishness effect of $b^* \leq -30$ is exhibited when $0.05 \leq n \leq 0.7$ (B, G). However, hues that fall within $(|a^*|+|b^*|) \leq 70$ are exhibited in the range of $1.0 \leq m < 2.5$ (B) or $4.0 < m \leq 5.0$ (G).

Therefore, the ranges that provide a more preferred, greenish blue color of high chroma are $2.5 \leq m \leq 4.0$ and $0.05 \leq n \leq 0.7$ as mentioned above. In these ranges, the $a^*$ and $b^*$ values both had large values as negative values. Described specifically, with a pigment that the numbers m and n of the respective kinds of substituent groups in the phthalocyanine derivative represented by the formula (I) fall within the above-described, corresponding preferred ranges, $70 \leq (|a^*|+|b^*|)$ is achieved with $a^*$ and $b^*$ satisfying $a^* \leq -25$ and $b^* \leq -30$. By a detailed study conducted by the present inventors, it has also been confirmed that, in the above-described effective method by the control of the numbers of the respective kinds of substituent groups, increasing the number of sulfonic group is a method tending to increase bluishness. Problems were, however, confirmed to arise in that a gradual reduction occurs in chroma when the number n of substituent sulfonic group(s) exceeds 0.7, and dullness appears in greenishness along with a reduction in chroma when the number n of substituent sulfonic group(s) is set at 1 or greater.

In addition, differences between the pigment newly provided by the present invention and the blue pigment known and used conventionally (unsubstituted) were confirmed by a similar evaluation method as described above. As a result of a hue measurement of β-copper phthalocyanine which has already been put on the market and is known as a colorful blue pigment (PB15:3; "CHROMOFINE BLUE 4920", product name, purity: 96%, unsubstituted; product of Dainichiseika Color & Chemicals Mfg. Co., Ltd.), $L^*$ was 47.29, $a^*$ was −14.13, $b^*$ was −51.44, and as an index of chroma, $(|a^*|+|b^*|)$ was 65.57. From these values, the pigment provided by the present invention has been confirmed to have a still better greenish blue hue of high chroma among pigments of the same skeleton having high chroma likewise. Moreover, the present invention is not limited to having this feature as a characteristic, but also enables to provide a still better colorant that meets its application owing to the optimal control and adjustment of the numbers of phthalimide group(s) and sulfonic group as substituent groups in commensurate with the application.

As has been described above, the present invention has as a premise to control the numbers of the respective kinds of substituent groups in the compound represented by the formula (I) to the corresponding ranges specified in the present invention. To obtain an image recording material optimal to various recording methods, however, the followings are important. Described specifically, to stably obtain the effect that can realize a greenish blue hue of high chroma as desired in the present invention, it becomes important to elucidate indexical roles, which the numbers of phthalimidomethyl group(s) and sulfonic group as substituent groups on the metal phthalocyanine skeleton making up the pigment contained in the image recording material, in relation to its hue and to provide a technology that can more precisely perform a fine adjustment of the hue. In this connection, according to the features of the present invention, it is possible to perform a fine adjustment that shifts the maximum reflectance wavelength for the target phthalocyanine derivative to a long-wavelength side, in other words, to a greenish side compared with most-commonly used copper phthalocyanine (β-form, 465 nm±5 nm). As a result, the hue becomes greenish blue. According to a further study by the present inventors, particularly preferred is one having a maximum reflectance wavelength in a range of 460 nm to 500 nm in a visible range of 380 nm to 780 nm in its spectral reflectance spectrum, and this preferred one enables to provide a pigment more suited for a colorant desired in the present invention. According to a still further study by the present inventors, the elimination of impurities from a pigment to be used provides the pigment with an increased reflectance at its maximum reflectance wavelength, so that a colorful pigment having higher tinting power is provided. Accordingly, the above-mentioned control of the numbers of the respective kinds of substituent groups that make up the pigment according to the present invention is an effective adjustment method to hues corresponding to various applications, and at the same time, enables to adjust the maximum reflectance wavelength and reflectance. The adoption of the features specified in the present invention makes it possible to surely provide a pigment as a colorant that can more precisely achieve desired characteristics.

The colorant composition and image recording material according to the present invention, which are colorants obtainable by using the above-described pigment according to the present invention, are characterized by containing, as their pigment component, the pigment represented by the formula (I). As the pigment, one having high purity is particularly preferred as mentioned above. The pigment according to the present invention can record an image excellent in colorfulness, brightness, transparency and the like when eventually used as an image recording material (colorant). Further, these characteristics are expressed no matter whether the image recording material is in a solid form or in a liquid form. A description will next be made about a method for the production of the colorant composition and image recording material according to the present invention.

No particular limitation is imposed on a method for ultrafinely dividing the pigment represented by the formula (I) as required upon production of the colorant composition and image recording material according to the present invention, and a conventionally-known method can be used. Examples include a method that subjects the pigment to acid paste treatment and a method that performs ultrafine division by collision grinding or milling. The collision grinding method can be a dry milling method that uses a ball mill or oscillating mill, and grinding media such as steel balls or steel rods are used, and in addition, an inorganic salt may be used as a milling aid as needed. The milling method can be a salt milling method or a solvent milling method, and an inorganic acid such as anhydrous sodium sulfate, sodium chloride or aluminum sulfate is used as a milling aid. The fine particulate pigment obtained as described above has a hue having colorfulness, brightness and transparency, and also exhibits excellent properties with respect to various fastness or resistance properties, such as light fastness, heat resistance, solvent resistance, chemical resistance and water resistance, and negative electrostatic chargeability.

When a pigment is used for coloring a paint, plastic or the like, the average particle size of primary particles of the pigment is generally controlled large, for example, to a size of about 500 nm or greater to provide the pigment with performance such as hiding power, ready dispersibility in a medium, weatherability, and heat-resistant processability. However, a pigment having such a particle size is accompanied by a problem in that the transparency, brightness and colorfulness of its hue are lowered when used as a colorant in an image recording material.

Especially when the pigment is used as a colorant for image recording such as electrophotography, electronic printing, electrostatic recording, inkjet recording or thermal transfer recording, the pigment may not be considered to be sufficient in the transparency, brightness and colorfulness of its hue even when the particle size of its primary particles is controlled to still smaller 200 to 500 nm, and therefore, a problem such as the unavailability of colorful prints still remains unsolved. For such a reason, it is preferred to control the particle size of its primary particles to still finer 10 to 200 nm upon production of a pigment for use in the recording of images by such a recording method as mentioned above. When process aspects and economical aspects are taken into consideration, the control to ultrafine particles of 10 nm and smaller involve many problems in the production method and cost. Except for certain special applications, the control to 30 to 150 nm or so is, therefore, considered to be a preferred embodiment. An ultrafine particle size around 10 nm may, however, be required in some cases depending on the application, for example, when to be used for color filters or the like.

When the above-described pigment according to the present invention is used to produce a colorant composition for image recording (image recording material) with at least the pigment and a resin being contained therein, it is preferred to disperse the pigment by a usual dispersion method such as flushing, heated kneading or wet dispersion such that the size of particles dispersed in the resin is reduced to approx. 200 nm or smaller in terms of weight average particle size. Further, with the quality aspect, process aspect and economic aspect being taken into consideration, it is a more preferred embodiment to disperse the pigment in the resin such that the pigment is reduced to approx. 150 nm or smaller. Upon production of such a colorant composition, it is, therefore, preferred to use, as a pigment to be dispersed, one that has been ultrafinely divided beforehand to have the above-described dispersed particle size.

For providing an image with a color of still better properties, such as transparency, brightness, colorfulness and negative electrostatic chargeability, and also with still better physical properties when the colorant composition according to the present invention is used as an image recording material, the pigment to be used may preferably be one that has been subjected to post-treatments such as those to be described below. Described specifically, the pigment according to the present invention as represented by the formula (I), said pigment being to be used in this case, may preferably be one that has been subjected according to conventionally-known methods to such post-treatments as controlling pigment crystals and controlling the shape and particle size of pigment particles to desired ranges.

In the pigment represented by the formula (I) and characterizing the present invention, the range of the number (m) of phthalimidomethyl group(s) is $1.0 \leq m \leq 5.0$, the range of the number (n) of sulfonic substituent group is $0.05 \leq n \leq 1.0$, and further, M represents a liganded or unliganded metal atom, a metal oxide, or two hydrogen atoms, all, as described above. An embodiment of the greenish blue pigment according to the present invention can be prepared by singly using a pigment that satisfies the above-described requirements or by combining pigments of different ranges from those satisfying the above-described requirements. Without being limited to such an embodiment, it is also a preferred embodiment to prepare the greenish blue pigment according to the present invention by making the combined use of a pigment one or both of the substituent groups of which do not fall within in the above-described, corresponding range or ranges. In this case, the pigment represented by the formula (I) may account for 50 mass % or more, preferably 70 mass % or more of the entire pigment mass. When prepared as described above, it is possible to provide a pigment that can exhibit a greenish blue hue of high chroma. This means that the single use of the pigment represented by the formula (I) and satisfying the requirements specified in the present invention is most preferred in cost and manufacture in the preparation of a desired pigment and that, when a fine adjustment is needed to provide a pigment of a hue more suited to an application purpose, the combined use of another pigment the number or numbers of one or both of the substituent groups of which do not fall within the corresponding range or ranges specified in the present invention, to say nothing of the combined use of another pigment the number or numbers of one or both of the substituent groups of which is or are within the corresponding range or ranges specified in the present invention, can perform fine adjustments, for example, of transmittance, spectral reflectance peak wavelength, and the like.

Further, under conditions that do not impair the properties possessed by the phthalocyanine pigment as a base, the pigment according to the present invention may be prepared, for example, by using it together and in combination with a phthalocyanine pigment of another structure. This method is preferred in that various physical properties can be effectively achieved depending on the combination of pigments. This case, however, involves the combined use of another pigment that does not meet the conditions of the formula (I) as specified in the present invention, and this another pigment is, therefore, required to be limited to a range that does not impair the effect of providing a pigment that exhibits a greenish blue hue of high chroma as intended in the present invention. Described specifically, the another pigment should be selected exclusively for use to achieve a purpose such as a fine adjustment of hue under conditions that maintain the effects as intended in the present invention. Similar to the above-mentioned case in which the pigment one or both of the substituent groups of which does or do not fall within the corresponding range or ranges specified by the formula (I) is combined, such another pigment is used as a color-matching pigment.

When using the colorant composition of the present invention as an image recording material, the pigment represented by the formula (I) specified in the present invention is prepared alone, or in addition to the pigment represented by the formula (I), a color-matching pigment to be used in combination with the above-mentioned pigment is also prepared, and the colorant composition is produced using the pigment represented by the formula (I) singly or in combination with the color-matching pigment. These pigments may be mixed together or formed into a solid solution beforehand, or may be mixed together in a production step of the colorant composition for image recording. Although no particular limitation is imposed on the production method of the colorant composition for image recording, the following production methods can be mentioned as examples, and these methods are all usable. Described more specifically, there is a method that directly produces a colorant composition, which contains the pigment represented by the formula (I) singly or in combination with a pigment not included in those represented by the formula (I) at concentrations suited for the image recording material, by using the pigment represented by the formula (I) singly or a mixed fine-powder pigment, a fine-powder solid-solution pigment or the like, which has been obtained by conducting color matching with the pigment not included in those represented by the formula (I), in a pigment production step. There is another method that produces a colorant composition, which contains the pigment represented by the formula (I) at a high concentration, with the above-described mixed fine-powder pigment or the like by using a heated kneading machine such as a roll mill or extruder beforehand, or with a press cake or the like of the pigment represented by the formula (I) alone or a mixed pigment of the pigment represented by the formula (I) and another pigment not included in those represented by the formula (I) by using a heated kneader or the like. As a further alternative, it is also possible to use a method that disperses the pigment represented by the formula (I) alone or a mixed pigment of the pigment represented by the formula (I) and another pigment not included in those represented by the formula (I) in a polymerization reaction mixture of one or more monomers used to make up a resin, and then polymerizes the monomer or monomers to incorporate the pigment or pigment mixture in the resulting resin (polymer).

Described more specifically, examples of the methods for the production of the high-concentration colorant composition, which contains the pigment represented by the formula (I), include various methods such as those to be described below.

(A) Production methods of a high-concentration colorant composition containing the pigment represented by the formula (I) and making use of a color-matching pigment:

(a) The individual pigments to be used are separately dried and then subjected to collision grinding or milling. A mixture of the resulting individual fine-powder pigments and a resin are kneaded by a heated kneading machine to obtain the high-concentration colorant composition.

(b) Wet press cakes of the individual pigments to be used are mixed, and subsequent to drying, are subjected to collision grinding or milling. The resulting, mixed fine-powder pigment and a resin are kneaded by a heated kneading machine to obtain the high-concentration colorant composition.

(c) Wet press cakes of the pigments (1) and (2) to be used and a resin are charged in a heated kneader or the like, and are then subjected to fusion flushing or the like to produce the high-concentration colorant composition.

(d) Wet press cakes of the pigments (1) and (2) to be used are mixed together beforehand, and using the resulting pigment mixture, the high-concentration colorant composition is produced in a similar manner as the above-described method (c).

(e) Fine powders of the pigments (1) and (2) to be used, a resin and a small amount of water are charged in a heated kneader, and are then subjected to fusion flushing or the like to produce the high-concentration colorant composition.

(f) The mixed fine-powder pigment used in the above-described method (a) or (b), a resin and a small amount of water are charged in a heated kneader, and are then subjected to fusion flushing or the like to produce the high-concentration colorant composition.

The resin such as a thermoplastic polymer resin or wax to be used for the production of the colorant composition, which is useful in the image recording material according to the present invention, is not limited in particular, and functions as a dispersant when the colorant composition is used in a solid form or as a dispersant for the pigment or pigments when the colorant composition is used in a liquid form. When the colorant composition is actually used as a recording material, the resin acts as a binder for the pigment or pigments.

As the resin to be used for such purposes as mentioned above, any resin can be used insofar as it has been conventionally used in a dry developer for electrophotography, electrostatic printing, electrostatic recording or the like, an oil-based or water-based inkjet ink, or an image recording material such as a thermal transfer ink ribbon or film, and no particular limitation is imposed thereon. In addition, conventionally-known additives, for example, a charge control agent, a fluidizing agent and/or as a medium, a solvent, water-based medium or the like can also be used as needed depending on the above-described individual applications.

The colorant composition according to the present invention, which is useful for recording images, can be either one produced from the beginning to have a pigment concentration suited for an image recording material as its application purpose or one produced as a high-concentration colorant composition with the pigment contained at a high concentration. The high-concentration colorant composition contains the pigment at the high concentration and, when thoroughly milled beforehand to disperse the pigment for color matching, can facilitate the subsequent production steps for the image recording material. The high-concentration colorant composition is used in a desired solid, paste or liquid form such as coarse particles, a coarse powder, a fine powder, a sheet or small aggregates. The content of the pigment in the composition may be generally 10 to 70 mass % or so, preferably 20 to 60 mass % or so.

To the image-recording colorant composition according to the present invention, one or more of conventionally-used, various additives, solvents and the like are added depending on each application purpose, whereby the image-recording colorant composition is used as an intended image recording material. Examples of the image recording material include so-called, fine powdery, dry developers, electrostatic recording materials, inkjet recording inks, and thermal transfer ink ribbons and films with the colorant composition coated on substrates such as films or paper, and the like.

The content of the pigment in the image-recording colorant composition according to the present invention, which contains the pigment at a concentration suited for an image recording material as an application purpose, differs depending on the application purpose of the composition, and no particular limitation is imposed thereon. For example, the content of the pigment in the whole colorant composition, which includes the pigment of the present invention represented by the formula (I) and color-matched in a cyan color alone or a mixed pigment containing the pigment represented by the formula (I), a resin, and one or more of other additives and media, may generally be 2 to 20 mass % or so. When used as a dry recording material or the like for electrophotography, the content of the pigment may be 2 to 15 mass % or so, with 3 to 10 mass % or so being preferred. When used as a colorant in a thermal transfer ink ribbon or film, the content of the pigment may be 4 to 15 mass % or so, with 6 to 10 mass % or so being preferred. When used as an inkjet recording ink, on the other hand, the content of the pigment may be 3 to 20 mass % or so, with 5 to 10 mass % or so being preferred. The pigment is, therefore, used at a most preferred content depending on each application purpose.

As methods for the production of the above-described high-concentration colorant composition of the pigment, there are, for example, a heated kneading dispersion method as a dry method and a media dispersion method, which uses ceramic beads, glass beads, steel balls or the like, as a wet method. Especially as a method for dispersing the pigment at a high concentration in a resin, it is common to use a method that melts the resin and kneads and disperses the pigment by using a kneading disperser such as a two-roll mill, three-roll mill, heated kneader, heated press kneader, single-screw extruder or twin-screw extruder. In each of these methods, it is desired to conduct the kneading dispersion processing at a temperature of 120° C. or lower. By conducting the kneading dispersion under processing temperature conditions of such a relatively low temperature, the particle size of the pigment which has been ultrafinely controlled beforehand is maintained, as it is, in the composition. By also conducting, at temperature conditions of 120° C. or lower, the subsequent processing step for the production of an image recording material, the resulting image recording material can exhibit a colorful, bright and transparent hue.

As a method for dispersing the pigment at a high concentration, the most preferred method is a method that flushes a water-based paste of the pigment with a molten resin (an atmospheric melt flushing method), for example, the method proposed in JP-A-2-175770 or a like method. Described specifically, this method first charges a wet press cake of the pigment and a resin binder without using any solvent in a kneader or flusher that can be heated with steam, then conducts kneading at a temperature lower than the melting point or softening point of the resin under atmospheric pressure to have the pigment transferred from a water phase into a resin phase, eliminates the separated water, and further, evaporates any remaining water by kneading. This method has features that the use of the wet press cake makes it possible to have the pigment particles transferred, as they are, from the press cake into the resin and the kneading dispersion processing is allowed to proceed at temperatures not higher than 100° C. as long as water exists. As another preferred method for dispersing the pigment at a high concentration, the high-concentration colorant composition can also be obtained by a method that adds water as a dispersion medium to the powdered pigment and resin binder, and in a similar manner as the above-described method, conducts kneading at atmospheric pressure in the absence of any solvent while controlling the processing temperature at a temperature not higher than 120° C. and lower than the melting point or softening point of the resin, thereby having the pigment transferred into a resin phase, eliminating the separated water, and evaporating any remaining water by kneading.

By using the image-recording colorant composition according to the present invention, various image recording materials such as a dry developer for electrophotography, electrostatic printing, electrostatic recording or the like, a water-based, oil-based or solid inkjet recording ink, a thermal transfer ink ribbon and a thermal transfer ink film can be produced by such methods as will be described below. For example, each image recording material can be produced by using the above-described compound (pigment) represented by the formula (I) singly or a composition, which has been obtained by preparing a color-matched pigment with another pigment such that the color-matched pigment had a pigment concentration suited for the corresponding application from the beginning, as it is, or dispersing or diluting and redispersing the above-described high-concentration colorant composition, in which the above-described pigment is dispersed at a high concentration in a resin, in a resin binder, resin solution or addition-polymerizable monomer, and then following a process known per se for the production of the image recording material. Here, one or more of a conventionally-known charge control agent, fluidizing agent, ferromagnetic material, solvent medium, water-based medium and the like may be added as needed to produce an image recording material with such additive or additives incorporated therein.

As a representative image recording material, one produced by such a production method as described below is used. An outline of the production method will be described hereinafter. A dry recording material is used, for example, as an image recording material for use in electrophotography, electrostatic printing, electrostatic recording, or the like. Employed as the dry recording material is a fine powdery, dry developer produced by a production method or process such as a grinding method or a suspension polymerization process, an emulsion polymerization and aggregation process or the like, which is called "a polymerization process". Here, the grinding method is a production method that heats and kneads the pigment, a resin binder, a charge control agent and the like, and subsequent to cooling, the resulting kneaded mass is ground and classified to a predetermined particle size, and the suspension polymerization process is a process that forms an addition-polymerizable monomer, in which the pigment, a charge control agent and the like have been dispersed, into an o/w emulsion with controlled sizes of droplets and forms the addition-polymerizable monomer into a colored, fine particulate polymer by suspension polymerization. Further, the emulsion polymerization and aggregation process is a process that mixes a fine dispersion of the pigment and a charge control agent in an emulsion polymerization mixture, and heats the resulting colored emulsion polymerization mixture to induce cohesion and aggregation, whereby the pigment and charge control agent are coprecipitated and adsorbed on polymer particles and at the same time, the resulting aggregates are microparticulated to a predetermined particle size. In each of these method and processes, one or more of conventionally-known materials such as fluidizing agents and ferromagnetic materials may be added further as needed.

As a cyan image recording material, the image-recording colorant composition according to the present invention can be used with a distinct color such as a monochromatic color, dichromatic color or multichromatic color. Without being limited to this, the image-recording colorant composition according to the present invention can be of course used, as a full-color recording system, together or as a set with image recording materials of magenta and yellow and optionally further, black. Examples of organic pigments and inorganic pigments usable in these cases include conventionally-used pigments such as phthalocyanine-based, azo-based, polycondensation azo-based, azomethineazo-based, anthraquionone-based, perinone- and perylene-based, indigo- and thioindigo-based, dioxazine-based, isoindolinone-based, pyrrolopyrrole-based, and like pigments; carbon black pigments; titanium oxides; iron oxides; baked pigments; and extender pigments.

Especially as pigments usable in full-color image recording materials, representative examples include, as magenta pigments, quinacridone-based red pigments; as yellow pigments, individual azo-based, polycondensation azo-based, anthraquinone-based and isoindolinone-based yellow pigments; and as black pigments, carbon black pigments, azomethineazo-based black pigments, and black pigments obtained by color matching of pigments of various colors.

Similar to the color-matching pigment used in combination with the pigment represented by the formula (I) and characterizing the present invention, it is also preferred to use each of the above-enumerated various pigments as a pigment the particle size of which has been adjusted to approx. 200 nm or smaller, preferably approx. 150 nm or smaller in terms of the average particle size of primary particles by dispersing the pigment in a resin in accordance with a usual dispersion method for the production of the image-recording colorant composition, such as flushing, heated kneading or wet dispersion. The preparation of the pigment with an excessively fine particle size, however, results in very difficult dispersion, and requires long time for a dispersion step. It is, therefore, preferred to adjust the particle size to approx. 30 nm or greater. The above-described particle size is not absolutely needed, and a particle size around 10 nm may be preferred in some instances, for example, in applications for color filters and the like.

EXAMPLES

The present invention will next be described more specifically based on examples, a referential example and comparative examples of pigments. It is to be noted that the designations of "parts" and "%" herein are all on a mass basis. The followings are evaluation methods for pigments according to the present invention and the copper phthalocyanine pigments of the comparative examples. It is to be noted that PB15:3 employed extensively as a conventional blue pigment was chosen as a referential example.
(Evaluation Testing Methods for Baking Paints)
According to a formula containing the copper phthalocyanine derivative (4 parts) of each example or referential example, an aminoalkyd resin ("AMILAC 1026", product of Kansai Paint Co., Ltd.) (16 parts) and a thinner (10 parts), dispersion was conducted for 60 minutes by a paint conditioner to prepare a deep color paint. The hue of the paint and its dispersibility by a grind gauge were evaluated. Further, the copper phthalocyanine derivative was diluted with a white paint, which contained titanium oxide, such that the ratio of the derivative to titanium white became 1:20, and the tinting power of the derivative was visually determined.
(Evaluation Testing Methods for Colored Resins)
The copper phthalocyanine derivative pigment (40 parts) of each example or referential example and a polyester-based resin (60 parts) were kneaded at approx. 100° C. by a table-top kneader to prepare a pigment master batch. After the thus-prepared master batch (2.95 parts), the polyester-based resin (32.05 parts) and xylene (65 parts) were mixed, glass beads of 1 mm in diameter (100 parts) were added, and the resulting mixture was processed for 2 hours in a paint conditioner to prepare a coating formulation. After the thus-obtained coating formulation was spread by a bar coater #14 on black-coated art paper, the black-coated art paper was allowed to naturally dry for approx. 1 hour. Using the resultant black-coated art paper, its reflection density measurement and spectral reflectance measurement (chromaticy) were conducted by the methods to be described hereinafter.
Measurement of Reflection Density
As each reflection density, the Macbeth density value (cyan color) was measured by using a Macbeth reflection densitometer manufactured by Gretagmacbeth GmbH. It is to be noted that the Macbeth density of conventional PB15:3 used as the referential example was 2.2.
Measurement of Spectral Reflectance, Chromaticy
Spectral reflectance was measured by a spectrophotometer ("CM3600d", manufactured by Konica Minolta, Inc.), and the L*, a* and b* values and C* value were calculated. The chroma C* value was calculated from the below-described equation. It is to be noted that the chroma C* of conventional PB15:3 used as the referential example was 53.35. From the respective values, the following evaluation can be made.

$$C^* = \sqrt{(a^*)^2 + (b^*)^2}$$

L* lightness: blacker as L* becomes closer to 0, and whiter as L* becomes closer to 100.
a*: more greenish as a* becomes more negative, reduced in colorfulness as a* becomes closer to 0, and more reddish as a* becomes more positive.
b*: more bluish as b* becomes more negative, reduced in colorfulness as b* becomes closer to 0, and more yellowish as b* becomes more positive.
a*, b*: higher in chroma as the absolute values of a* and b* each become greater.

Example 1

To 2% fumed sulfuric acid (480 parts), crude copper phthalocyanine (30 parts), paraformaldehyde (15.8 parts) and phthalimide (45.8 parts) were gradually added while maintaining a temperature not higher than 55° C., followed by stirring for 30 minutes until dissolution. The reaction mixture was heated over 1 hour to 70° C., and a reaction was then conducted at 70 to 75° C. for 7 hours. After completion of the reaction, the reaction mixture was poured into water (2,000 parts) for precipitation. The resulting slurry was heated at 90° C. for 30 minutes, and was then filtered. The thus-obtained filter cake was washed with water until neutral, and was then dried at 100° C. for 12 hours. The product had a purity of 80.0%, and contained 2.3 phthalimidomethyl groups (m) and 0.06 sulfonic group (n). The product was deflocculated in its entirety in a mixture of water (1,500 parts) and soda ash (15 parts). Subsequent to stirring under heat at 50° C. for 2 hours, the product was collected by filtration, washed with water, and dried. The purity of the product was 98.9%.

On the copper phthalocyanine derivative obtained as described above, evaluation was conducted by the above-described baking paint testing method. It was confirmed that one excellent in all of dispersibility, hue and tinting power, especially of high quality with respect to tinting power compared with conventional PB15:3 as the referential example was obtained. Next, as a result of evaluation by the above-described colored resin testing method, the Macbeth density was 1.75, the chroma (C*) was 53.37, L* was 52.0, a* was −19.2, and b* was −49.8. In particular, the hue was sufficiently greenish and colorful compared with conventional PB15:3 as the referential example although it was a little reddish compared with that of the below-described derivative of Example 2.

Example 2

To 100% sulfuric acid (354 parts), crude copper phthalocyanine (30 parts) was added little by little while maintaining a temperature not higher than 55° C., followed by stirring for 30 minutes until dissolution. Subsequently, hydroxymethylphthalimide (50.6 parts) and acetic anhydride (29.7 parts) were added. The reaction mixture was heated over 1 hour to 70° C., and a reaction was conducted at 70 to 75° C. for 6 hours. After completion of the reaction, water (2,000 parts) was added for precipitation, and the resulting slurry was filtered. The thus-obtained filter cake was washed with water, and was then dried at 100° C. for 12 hours to obtain a product (66.0 parts). The product contained, as average numbers of substituent groups, 3.05 phthalimidomethyl groups (m) and 0.05 sulfonic group (n) and exhibited a colorful, bluish green color, but its tinting power was a little inferior because its purity was 82.3%, that is, a little low. The product was deflocculated in its entirety in water (1,500 parts), and soda ash (15 parts) was added. Subsequent to stirring under heat at 50° C. for 2 hours, the product was collected by filtration, washed with water, and dried. As a result, a dry product (54.9 parts) having a purity of 99.9% was obtained.

On the dry product obtained as described above, a baking paint test was next conducted as in Example 1. As a result, it was confirmed that the hue became more colorful and one having excellent quality in all of dispersibility, hue and tinting power was obtained. On its tint, evaluation was also conducted as in Example 1. The Macbeth density was 1.66, the chroma (C*) was 51.37, L* was 55.04, a* was −26.09, and b* was −44.25. The dry product was more toned down in redness more toned down in reddishness compared with the one obtained in Example 1, and exhibited a greenish blue hue of high chroma.

Example 3

To 100% sulfuric acid (354 parts), crude copper phthalocyanine (30 parts) was added little by little while maintaining a temperature not higher than 55° C., followed by stirring for 30 minutes until dissolution. Subsequently, hydroxymethylphthalimide (33.7 parts) and acetic anhydride (19.4 parts) were added. The reaction mixture was heated over 1 hour to 100° C., at which a reaction was conducted for 5 hours. After completion of the reaction, the reaction mixture was cooled to 70° C. under stirring, water (2,000 parts) was added for precipitation. The resulting slurry was heated at 90° C. for 30 minutes, and then filtered. The thus-obtained filter cake was washed with water until neutral, and was then dried at 100° C. for 12 hours to obtain a colorful bluish green product (59.6 parts). The purity of the thus-obtained product was 95.9%. As the average numbers of substituent groups, 3.2 phthalimidomethyl groups (m) and 0.48 sulfonic group (n) were contained.

On the thus-obtained product, a baking paint test was next conducted as in Example 1. As a result, the compound was confirmed to be one having excellent quality in all of dispersibility, hue and tinting power. On its tint, evaluation was also conducted as in Examples 1 and 2. The Macbeth density was 2.10, C* was 50.22, L* was 53.53, a* was −38.10, and b* was −32.72. The product exhibited a greenish blue hue of high chroma.

Example 4

To 100% sulfuric acid (354 parts), crude copper phthalocyanine (30 parts) was added little by little while maintaining a temperature not higher than 55° C., followed by stirring for 30 minutes until dissolution. Subsequently, hydroxymethylphthalimide (45.0 parts) and 20% fumed sulfuric acid (267 parts) were added. The reaction mixture was heated over 1 hour to 70° C., and a reaction was conducted at 70 to 75° C. for 5 hours. After completion of the reaction, the reaction mixture was poured into water (1,500 parts) for precipitation. The resulting slurry was heated at 90° C. for 30 minutes, and then filtered. The thus-obtained filter cake was washed with water until neutral, and was then dried at 100° C. for 12 hours. The purity of the product was 96.1%, and 3.1 phthalimidomethyl groups (m) and 0.8 sulfonic group (n) were contained.

On the thus-obtained product, a baking paint test was conducted as in Example 1. As a result, the product was confirmed to be one having excellent quality in all of dispersibility, hue and tinting power. On its tint, evaluation was also conducted as in Example 1. The Macbeth density was 1.60, C* was 49.88, L* was 50 or greater, a* was −40.3, and b* was −29.4. The product exhibited a greenish blue hue of high chroma.

Example 5

In a similar manner as in Example 3 described above, hydroxymethylphthalimide and acetic anhydride were reacted in adjusted amounts to obtain a product having a purity of 96.3%. As the average numbers of substituent groups in the thus-obtained product, 4.2 phthalimidomethyl groups (m) and 0.08 sulfonic group (n) were contained. A baking paint test was also conducted as in Example 1. As a result, the product was confirmed to be one having excellent quality in all of dispersibility, hue and tinting power. On its tint, evaluation was also conducted as in Example 1. The Macbeth density was 1.61, C* was 49.73, L* was 50 or greater, a* was −31.1, and b* was −38.8. The product exhibited a greenish blue hue of high chroma.

Example 6

To 2% fumed sulfuric acid (250 parts), crude copper phthalocyanine (15.7 parts) was added little by little while maintaining a temperature not higher than 55° C. Under stirring, the reaction mixture was heated to 90° C. at a ramp-up rate of 1° C. per minute, and a reaction was conducted at 90 to 95° C. for 1.5 hours. Subsequently, the reaction mixture was cooled to 80° C., hydroxymethylphthalimide (15.7 parts) was added, and a reaction was conducted at 83 to 87° C. for 2.5 hours. After the reaction, the reaction product was collected by filtration, washed with water until neutral, and then dried at 100° C. for 12 hours. The purity of the product was 89.5%, and as the average numbers of substituent groups, 1.5 phthalimidomethyl groups (m) and 0.7 sulfonic group (n) were contained. The product was then deflocculated in its entirety in a mixture of water (1,500 parts) and soda ash (15 parts). Subsequent to stirring under heat at 50° C. for 2 hours, the product was collected by filtration, washed with water, and dried to obtain a dry product. The purity of the product was 98.2%.

On the thus-obtained dry product, a baking paint test was conducted as in Example 1. As a result, it was confirmed that one having excellent quality in all of dispersibility, hue and tinting power was obtained. On its tint, evaluation was also conducted as in Example 1. The Macbeth density was 1.78, C* was 47.38, L* was 50 or greater, a* was −26.02, and b* was −39.6.

Comparative Example 1

To 100% sulfuric acid (420 parts), crude copper phthalocyanine (30 parts) was added little by little while maintaining a temperature not higher than 55° C., followed by stirring for 30 minutes until dissolution. Subsequently, hydroxyphthalimide (54.9 parts) and 20% fumed sulfuric acid (127 parts) were added, the reaction mixture was heated over 1 hour to 70° C., and a reaction was then conducted at 70 to 75° C. for 6 hours. After completion of the reaction, the reaction mixture was poured into water (1,500 parts) for precipitation. The resulting slurry was heated at 90° C. for 30 minutes, and then filtered. The thus-obtained filter cake was washed with water until neutral, and was then dried at 100° C. for 12 hours. The purity of the product was 70%. 1.9 phthalimidomethyl groups (m) were contained, but no sulfonic group (n) was practically detected. On the thus-obtained product, a baking paint test was conducted as in the respective examples. As a result, it was confirmed that the quality was clearly inferior in all of dispersibility, hue and tinting power compared with the products obtained in the respective examples. On its tint, evaluation was also conducted as in the examples. The Macbeth density was 1.4 or lower, so that the product of this comparative example was evidently lower in reflection density than those of the examples. Further, C* was 45 or lower, L* was 45 or lower, a* was −20 or greater, and b* was −40 or smaller. Accordingly, the product of this comparative examples was inferior in chroma to those of the examples, and did not exhibit a greenish blue color of high chroma as intended in the present invention.

Comparative Example 2

To 100% sulfuric acid (354 parts), crude copper phthalocyanine (30 parts) was added little by little while maintaining a temperature not higher than 55° C., followed by stirring for 30 minutes until dissolution. Subsequently, hydroxymethylphthalimide (73.9 parts) and acetic anhydride (42.6 parts) were added. The reaction mixture was heated over 1 hour to 70° C., and a reaction was conducted at 70 to 75° C. for 6 hours. After completion of the reaction, the reaction mixture was poured into water (2,000 parts) for precipitation. The resulting slurry was heated at 90° C. for 30 minutes, and then filtered. The thus-obtained filter cake was washed with water until neutral, and was then dried at 100° C. for 12 hours. The purity of the product was 76%. 3.9 phthalimidomethyl groups (m) were contained, but no sulfonic group (n) was practically detected. On the thus-obtained product, a baking paint test was conducted as in the respective examples. As a result, the quality of the product of this comparative example was clearly inferior in all of dispersibility, hue and tinting power compared with the products of the respective examples. Neither density nor color evaluation was hence conducted on the product of this comparative example.

Comparative Example 3

To 100% sulfuric acid (354 parts), crude copper phthalocyanine (30 parts) was added little by little while maintaining a temperature not higher than 55° C., followed by stirring for 30 minutes until dissolution. Subsequently, hydroxymethylphthalimide (56.3 parts) and acetic anhydride (33.0 parts) were added. The reaction mixture was heated to 70° C. over 1 hour, and a reaction was conducted at 70 to 75° C. for 7 hours. The reaction mixture was heated to 100° C., and a reaction was conducted at 100 to 105° C. for 5 hours. After completion of the reaction, the reaction mixture was cooled to 70° C. under stirring, and was then poured into water (2,000 parts) for precipitation. The resulting slurry was heated at 90° C. for 30 minutes, and then filtered. The thus-obtained filter cake was washed with water until neutral, and was then dried at 100° C. for 12 hours. The purity of the product was 91.5%. 5.1 phthalimidomethyl groups (m) and 0.5 sulfonic group (n) were contained. On the thus-obtained product, evaluation was conducted as in the respective examples. No reflection density was obtained. In a baking paint test, the quality of the product of this comparative example was clearly inferior in all of dispersibility, hue and tinting power compared with the products obtained in the respective examples. No color evaluation was hence conducted on the product of this comparative example.

Comparative Example 4

A reaction was conducted as in Example 3 except that the amounts of hydroxymethylphthalimide and acetic anhydride were reduced from 33.7 parts and 19.4 parts to 9.01 parts and 5.19 parts, respectively. The purity of the resulting product was 96.4%. As the average numbers of substituent groups, 0.7 phthalimidomethyl group (m) and 0.6 sulfonic group (n) were contained. On the thus-obtained product, evaluation was conducted by a baking paint test as in the respective examples. The hue was greenish and dull, the tinting power was inferior. No color evaluation was hence conducted on the product of this comparative example.

Example 7

Evaluation Test of Inks for Inkjet Applications

Using a wet press cake of the phthalocyanine derivative obtained in Example 3, a water-based pigment dispersion of the formula shown in Table 1 was prepared by a horizontal media disperser. With the water-based pigment dispersion so obtained, an ink having a pigment concentration of 6% was prepared. After printing was performed with the thus-obtained ink on photographic glossy paper by a commercial inkjet printer, the color values and gloss values (20° and 60° gloss values) were measured by "EYEONE" (manufactured by X-Rite Asia Pacific Limited) and "MICRO-TRI-GLOSS" (manufactured by BYK-Chemie GmbH), respectively, and evaluation was then performed.

TABLE 1

Formula of Inkjet Recording Ink

| Components | Parts |
| --- | --- |
| Press cake of phthalocyanine derivative | 20.0 (pigment content 30%) |
| Styrene-methacrylic acid based resin | 5.0 |
| Ethylene glycol | 10.0 |
| Glycerin | 5.0 |
| Water | 60.0 |
| Total | 100.0 |

For comparison, copper phthalocyanine ("CHROMOFINE BLUE A-220JC", product of Dainichiseika Color & Chemicals Mfg. Co., Ltd.) was used as a comparison standard, and an ink making use of this pigment was prepared as "sample 1". Further, an ink making single use of the pigment obtained in Example 3 was prepared as "sample 2". In addition, an ink making use of a mixture of the pigment used in the above-described sample 2 and the pigment used in the above-described sample 1 was prepared as "sample 3". Described specifically, a 3/7 by mass mixture of the pigment obtained in Example 3 and "A-220JC" as the comparison standard was used in the sample 3.

The inks, which had been obtained as the samples 1 to 3 as described above, were each evaluated by the color values of the pigments used in the respective inks and the gloss values of images printed with those inks on the photographic glossy paper. Assuming that the gloss values of the comparison standard were both 100, the gloss values were compared relative to those of the comparison standard. As shown in Table 2, the evaluation results of the color values of the respective pigments were directly reflected in their applications, and the samples 2 and 3, in which one of the pigments of the examples of the present invention was used, were confirmed to provide images of a still better greenish blue color and high chroma compared with the sample 1 in which the existing pigment chosen as the comparison standard was used.

TABLE 2

| | Color values | | Gloss value (relative comparison) | |
|---|---|---|---|---|
| | a* | b* | 20° | 60° |
| Sample 1 | −15.6 | −58.5 | 100 | 100 |
| Sample 2 | −36.1 | −37.7 | 156 | 115 |
| Sample 3 | −22.9 | −52.5 | 115 | 113 |

Sample 1 (comparison standard): copper phthalocyanine ("CHROMOFINE BLUE A-220JC", product of Dainichiseika Color & Chemicals Mfg. Co., Ltd.)
Sample 2: the copper phthalocyanine derivative of Example 3
Sample 3 (mixture): sample 2/sample 1 (Example 3/"A-220JC") = 3/7 by mass

Example 8

Phthalocyanine pigments having the structure specified in the present invention were prepared in a similar manner except for the use of crude zinc phthalocyanine and crude aluminum phthalocyanine with zinc and aluminum substituted, respectively, for the copper in the crude copper phthalocyanine used in the examples, and similar evaluations were conducted. As a result of comparisons with conventional PB15:3 used as the referential example, the phthalocyanine pigments were both confirmed to be of excellent quality in all of dispersibility, hue and tinting power. Further, no much relative differences in hue were observed depending on the differences of M in the structure represented by the formula (I) and making up the pigments, and the phthalocyanine pigments were each found to exhibit a greenish blue hue of high chroma as intended by the present invention. In particular, the pigment that M in the structure represented by the formula (I) was aluminum was by no means inferior to the pigment that M in the structure represented by the formula (I) was copper, and was excellent in colorfulness. From the standpoint of the stability as a production process, the weatherability of images formed, and the like, the pigment that M in the structure represented by the formula (I) is copper is preferred. However, the pigments may be different, for example, in dispersibility or the like depending on the differences of M in the formula (I). It is, therefore, preferred to select an optimal one from the Ms in the formula (I) as specified in the present invention while also taking into consideration a dispersant, resin, solvent and the like, which are selected depending on the application purpose of the pigment and are to be used in combination with the pigment. This means that the pigment specified in the present invention can be applied to a wider range because M in the formula (I) is not limited to copper.

INDUSTRIAL APPLICABILITY

According to the present invention, it is possible to provide a novel blue pigment that has resolved the drawbacks of the conventional cyan pigments for image recording materials, is excellent in safety, and exhibits a desired greenish blue hue of high chroma depending on the application. Further, the use of the greenish blue pigment of the present invention makes it possible to provide an excellent image recording material, which is suited for various recording methods the developments of which are pronounced to find wide-spread utility in recent years and which is free of any safety problem when disposed of. As a consequence, the formation of images of still higher quality is feasible by such various recording methods.

The invention claimed is:

1. A greenish blue pigment composition exhibiting a greenish blue hue of high chroma, the pigment composition comprising at least one pigment represented by following formula (I):

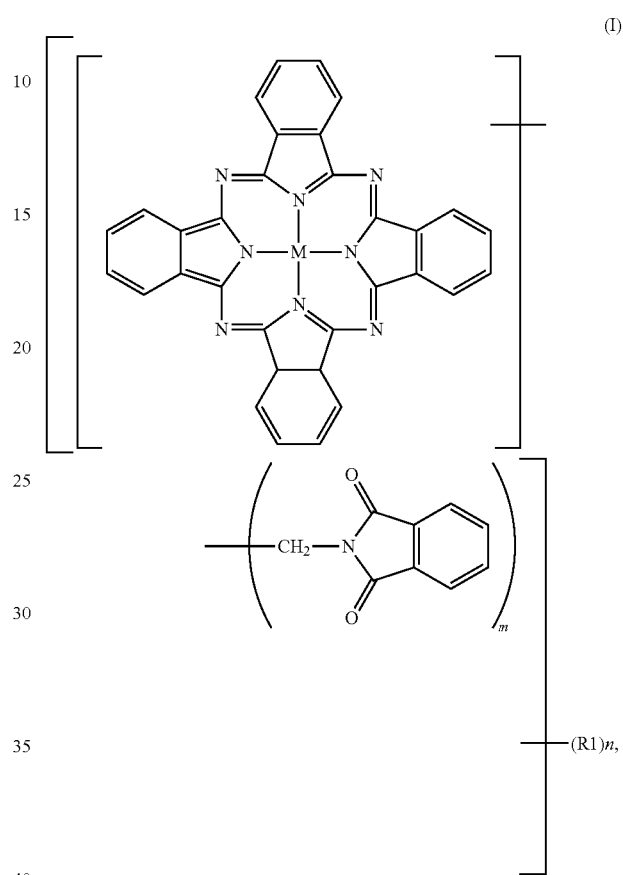

wherein m indicates a number of phthalimidomethyl group or groups, and m is in a range of $2.3 \leq m \leq 4.2$, R1 represents a sulfonic group, n indicates a number of the substituent group, and n is in a range of $0.05 \leq n \leq 0.8$, and M is a liganded or unliganded metal atom selected from the group consisting of Cu, Al, and Zn.

2. The greenish blue pigment composition according to claim 1, wherein the pigment represented by the formula (I) has a purity of at least 95.0%.

3. The greenish blue pigment composition according to claim 1, wherein in the formula (I), m is in a range of $2.5 \leq m \leq 4.0$ and n is in a range of $0.05 \leq n \leq 0.7$.

4. The greenish blue pigment composition according to claim 1, wherein in a spectral reflectance spectrum of the greenish blue pigment composition, a maximum reflectance spectrum in a visible light range from 380 nm to 780 nm exists in a range from 460 nm to 500 nm.

5. A colorant composition comprising at least a pigment and a resin, wherein the pigment comprises the greenish blue pigment composition according to claim 1.

6. An image recording material used in a recording method selected from the group consisting of electrophotography, electronic printing, electrostatic recording, and thermal transfer recording, comprising the colorant composition according to claim 5.

7. An image recording material for inkjet recording, comprising the colorant composition according to claim 5.

8. An image recording material for a color filter, comprising the colorant composition according to claim 5.

* * * * *